US012698529B2

(12) United States Patent
Prof Uhl

(10) Patent No.: US 12,698,529 B2
(45) Date of Patent: Aug. 4, 2026

(54) MICROSCOPE DEVICE

(71) Applicant: MILTENYI BIOTEC B.V. & CO. KG, Bergisch Gladbach (DE)

(72) Inventor: Rainer Prof Uhl, Bergisch Gladbach (DE)

( * ) Notice: Subject to any disclaimer, the term of this patent is extended or adjusted under 35 U.S.C. 154(b) by 486 days.

(21) Appl. No.: 18/270,873

(22) PCT Filed: Jan. 12, 2022

(86) PCT No.: PCT/EP2022/050491
§ 371 (c)(1),
(2) Date: Jul. 5, 2023

(87) PCT Pub. No.: WO2022/152720
PCT Pub. Date: Jul. 21, 2022

(65) Prior Publication Data
US 2024/0068026 A1 Feb. 29, 2024

(30) Foreign Application Priority Data
Jan. 12, 2021 (DE) ..................... 10 2021 100 350.4

(51) Int. Cl.
*G02B 21/16* (2006.01)
*C12Q 1/6874* (2018.01)
*G02B 21/36* (2006.01)
(52) U.S. Cl.
CPC ........... *C12Q 1/6874* (2013.01); *G02B 21/16* (2013.01); *G02B 21/361* (2013.01)
(58) Field of Classification Search
CPC ..... C12Q 1/6874; G02B 21/16; G02B 21/361
See application file for complete search history.

(56) References Cited

U.S. PATENT DOCUMENTS

2009/0309049 A1* 12/2009 Van Dijk .................. G01J 3/10
250/236

OTHER PUBLICATIONS

Advanced optical design for DNA sequencing systems (by Kirill Sobolev et al.) (Year: 2011).*

* cited by examiner

*Primary Examiner* — James A Dudek
(74) *Attorney, Agent, or Firm* — Jaquelin K. Spong

(57) ABSTRACT

The invention is directed to a microscope device comprising a microscope objective (1); one or more light sources; at least 3 dichroic beam sputters (50, 51, 56) and at least 2 cameras (109, 117) characterized in that the light generated by the light source interacts with the sample (3) thereby producing a sample beam (6), wherein—sample beam (6) is divided with a first dichroic beam splitter (50) into beam (K) and beam (L) wherein beam (K) and beam (L) have different spectral ranges of light and wherein—beam (K) is divided with a second dichroic beam splitter (51) into a first beam (A) having a first spectral range of light and a second beam (B) having a second spectral range of light and wherein first beam (A) is guided via reflection element (54) on the detector of the first camera (109) and wherein second beam (B) is guided via reflection elements (52) and (53) on the detector of the first camera (109) and wherein—beam (L) is divided with a third dichroic beam splitter (56) into a third beam (C) having a third spectral range of light and a fourth beam (D) having a fourth spectral range of light and wherein third beam (C) is guided via reflection element (58) and (59) on the detector of the second camera (117) and wherein the fourth beam (D) is guided via reflection element (57) on the detector of the second camera (117). Use of the microscope to obtain sequencing information.

16 Claims, 3 Drawing Sheets

MICROSCOPE DEVICE

BACKGROUND

The invention relates to a camera-based microscope which employs four-color distinction capabilities to provide a maximally contrast-rich fluorescence respectively transmitted light image.

Typically, camera detectors used in microscopy are monochrome. A multicolor microscope is disclosed in WO 2020/038752, which relates to a microscope device having dual emission detection capabilities. It employs two cameras and places a dichroic beam splitter into the finite optical space between the microscope and the two cameras, which record the two desired spectral regions. In order not to distort the transmitted spectral image, the dichroic is kept as thin and the reflection angle as small as possible. However, since a thin substrate tends to compromise flatness and hence the quality of the reflected image, an optimal thickness always reflects a compromise between the quality of the transmitted and the reflected image.

A similar technology is disclosed in US 2018/0067327 wherein an image beam is divided by a dichroitic beam splitter into two desired spectral regions which are then guided onto one camera.

SUMMARY

It is an object of the invention to provide for a microscope device capable of separating four spectral regions with two cameras only.

Object of the invention is therefore a microscope device comprising a microscope objective (1); one or more light sources; at least 3 dichroic beam splitters (50, 51, 56) and at least 2 cameras (109, 117) characterized in that the light generated by the light source interacts with the sample (3) thereby producing a sample beam (6), wherein sample beam (6) is divided with a first dichroic beam splitter (50) into beam (K) and beam (L) wherein beam (K) and beam (L) have different spectral ranges of light and wherein beam (K) is divided with a second dichroic beam splitter (51) into a first beam (A) having a first spectral range of light and a second beam (B) having a second spectral range of light and wherein first beam (A) is guided via reflection element (54) on the detector of the first camera (109) and wherein second beam (B) is guided via reflection elements (52) and (53) on the detector of the first camera (109) and wherein beam (L) is divided with a third dichroic beam splitter (56) into a third beam (C) having a third spectral range of light and a fourth beam (D) having a fourth spectral range of light and wherein third beam (C) is guided via reflection element (58) and (59) on the detector of the second camera (117) and wherein the fourth beam (D) is guided via reflection element (57) on the detector of the second camera (117).

Such microscope devices are especially useful for detecting multiple spectral ranges emitted by a sample which is often the case in sequencing DNA/RNA molecules. To avoid damaging of the sample, the interaction between the light and the sample should be kept as short as possible. Since the device of the invention can detect at least 4 different spectral ranges simultaneously, the use of the microscope device as disclosed herein in a sequencing-by-synthesis process it is a further object of the invention.

DETAILED DESCRIPTION

Figure 1:
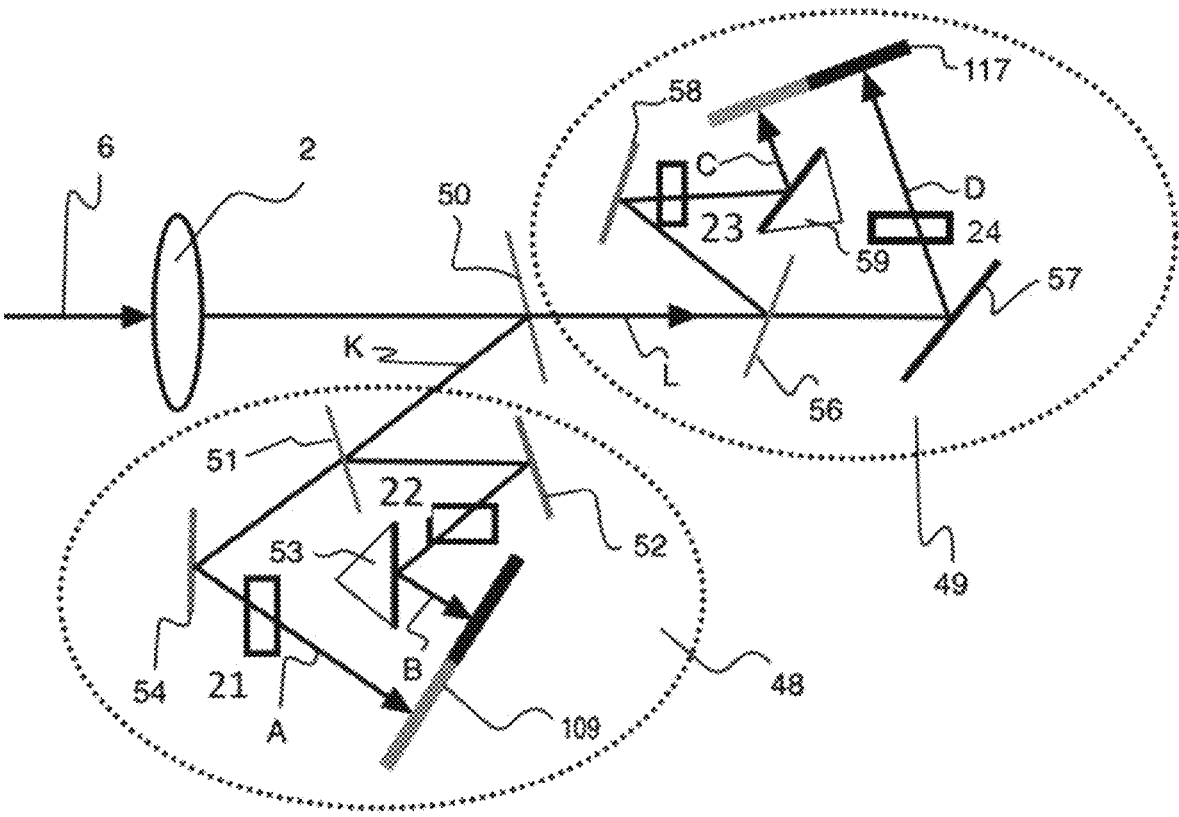
FIGS. 1 and 2 show two embodiments of the path of light of the microscope of the invention
Figure 2:
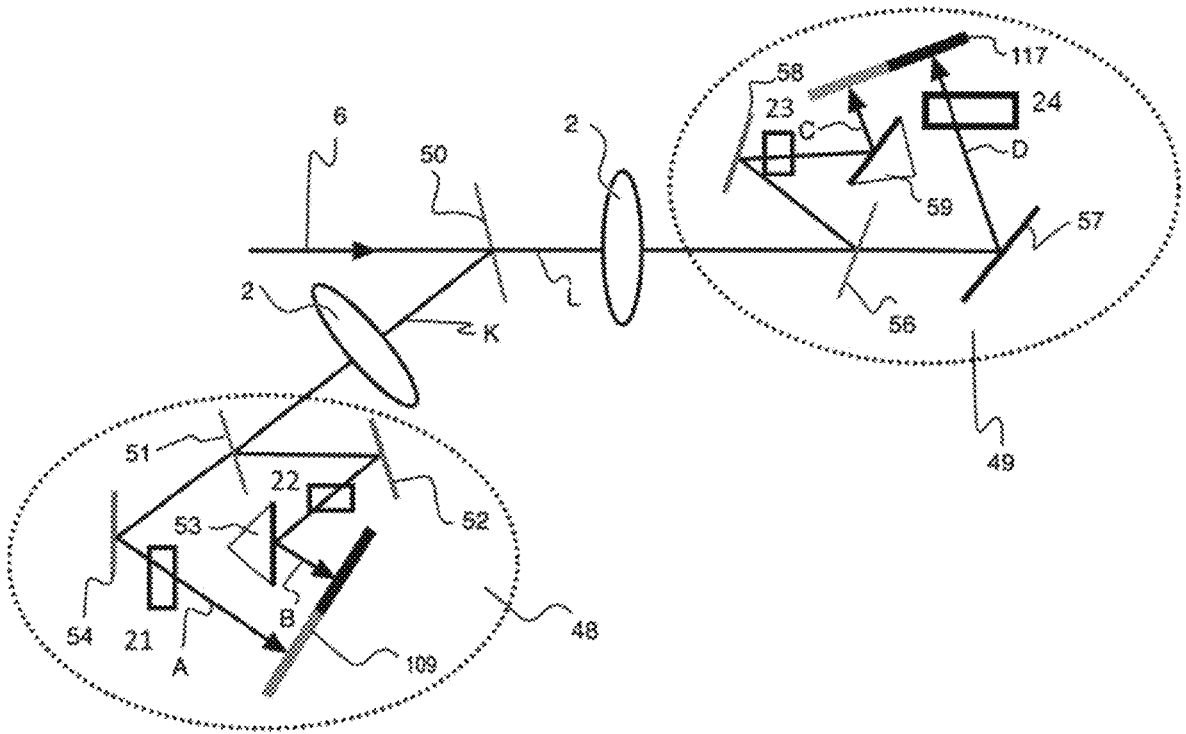
Figure 3:
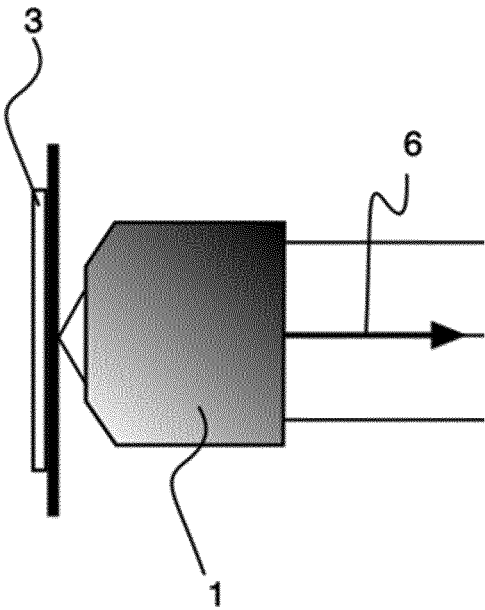
FIG. 3 shows a part of the device upstream of sample beam (6)

In the device of the invention as shown in FIG. 1 or 2, light originating from the sample (either transmitted or emitted) is separated into four spectral regions by three dichroic beam splitters, and the resulting image beams A, B, C and D are directed to two cameras (109, 117), whereby each of the two cameras records two spectral regions side-by-side on its sensor-chip. This is facilitated by the fact that high-end camera chips are available for image fields much bigger (for example 36×24 mm) than the image field of current microscopes, which maximally covers a square field of 17×17 mm. Alternatively, TDI cameras are used.

The microscope according to the invention may comprise a at least one camera (109, 117) which is of charge-coupled device (CCD) type, electron-multiplying charge-coupled device (EM-CCD) type, complementary metal-oxide-semiconductor (CMOS) type, scientific complementary metal-oxide-semiconductor (CMOS) type, time delayed integration (TDI) type or a combination thereof.

Preferable, the microscope is equipped to detect four spectral ranges, for example 405, 488, 561 and 638 nm or 375 nm, 473 nm, 532 nm, and 660 nm. To this end, preferably the cut-on wavelengths are chosen to 488, 561 and 638 nm as to separate the emission into the four spectral regions between the excitation wavelengths. Preferable, the respective spectral ranges of light of the first, second, third and fourth beams (interchangeable with terms A, B, C, D) are between 473 nm and 532 nm; 532 nm and 594 nm, 594 nm and 660 nm; 633 nm and 660 nm. It should be noted that these spectral ranges of light are given by way of example and depend on the function of the beam splitters, i.e. are not necessary bounded to this sequence.

In a preferred embodiment, at least one of the dichroic beam splitters (50, 51, 56) is arranged (tiled) in the path of light as to minimize or avoid the chromatic error of the light detected by the cameras. Since the chromatic error depends on the spectral range/the wavelength of the light, the angular position of the dichroic beam splitters (50, 51, 56) may be same or different.

Accordingly, the tilt angles of first, second and third dichroic beam splitter (50, 51, 56) with the respective residual images may be independently between +45° and −45°, preferable independently between +30° and −30° or independently between +25° and −25°. or independently between +15° and −15°. In any case, the tilt angles of the first and third dichroic beam splitters (50, 56) with the respective residual beams may be in opposing directions.

The light sources preferable provide light having a spectral range of wavelengths of 300 to 1750 nm, preferable 300-800 nm like white light, laser light, or LED light. The sample may be subjected to the light "as is" or may be provided with fluorescence or phosphorescence agent to mark regions or interest. To avoid damaging the sample, preferable light sources producing light with longer wavelengths are used, such as 525 and 635 nm.

Accordingly, the sample beam may be or comprise fluorescence or phosphorescence radiation originating from the sample (3) or radiation transmitted or reflected by the sample (3).

Further, the microscope device may be provided with at least one focusing element (2) into the beam-path of the sample beam upstream of the first beam splitter (shown in FIG. 1). In alternative, two or more focusing elements (2) may be provided in the sample beam downstream of the first beam splitter as shown in FIG. 2.

The focusing elements may consist or comprise at one lens or at least one objective or a combination thereof.

In another embodiment, the microscope device according to the invention may be provided with one or more optical element (21, 22, 23, 24) into the beam-path of first, second, third and/or fourth image beams A, B, C, D. Such optical elements are capable of focal plane or image plane shift and can optionally be inserted and removed from the beam-paths with an appropriate device. Suitable optical elements have a higher refractive index than the surrounding medium and may consist of coated or uncoated glass or polymer. Further, the optical elements can be provided with a filter for chromatic correction of any optical distortion which caused by the dichromatic beam splitters FIGS. 1 and 2 show the device of the invention, which uses two identical optical arrangements (48) and (49) for each of the two camera-chips (109) and (117). A beam splitter (50), placed in the finite optical space between tube-lens (2) and the camera-chips (9) respectively (18), splits the image beam (6) into two beams (K=A+B) and (L=C+D). In the optical arrangement (48), beam splitter (51) splits K into beams A and B, whereas in optical arrangement (49) a beam splitter (56) splits L into beams C and D. The reflected beam (B) needs two more reflections at mirrors (52) and (53), whereas the transmitted beam (A) needs only one reflection at surface (54), before it reaches the detector (109). (L), the beam transmitted by dichroic (50) is split into (C) by being reflected at dichroic (56), and into (D), which is transmitted at dichroic (56). As in (48), the transmitted fraction (D), requires a single reflection at a reflecting element (57), whereas the reflected fraction (C) requires two more reflections at reflecting surfaces (58) and (59).

As described for the previous variant of the invention, all beams reflected by a dichroic beam splitter may carry ghost-image information. In FIGS. 1 and 2, this applies to spectral regions (A), (B) and (C), which need suitable band-pass filters in front of the detectors, or to overcome spatial restraints, suitable filter characteristics for reflecting surfaces (54), (52) respectively (53) and (58) respectively (59).

In order to minimize (mostly spherical, astigmatic, or comatic) aberrations, the tilt-angle of the two dichroic elements (50) and (51) is kept at about 25° and at opposing angles, as to compensate for chromatic aberrations.

The thickness of the dichroic beam splitters is kept as small as possible (usually 1-3 mm) as to minimize thickness-related aberrations in transmission, but thick enough to maintain flatness of the reflecting surfaces, which is of paramount importance for image quality of the reflected fraction of the beam. (FIG. 1). Alternatively, in order to minimize (mostly spherical, astigmatic, or comatic) aberrations, one dichroic element is positioned between the objective lens (1) and the focusing element (2), allowing for larger tilt angles (preferably 45°) at this dichroic position and allowing for larger thickness (usually 3 mm, possibly 1 mm to 5 mm).

All three spectral regions (A), (B) and (C), which have undergone reflections at dichroic elements, may carry ghost-images, resulting from reflections on the rear (exit) side of the respective dichroic beam splitters (50, 51 and 56). While these ghost-images usually contain less than 1% of the transmitted image information, this may still lead to significant image degradation in cases where the reflected signal is weak and the sum of the transmitted signals is large. The cure for this is to bring appropriate bandpass filters or optical elements (21, 22, 23 and 24) into the beam-path.

Further, the reflection element (52) and/or (53) may be provided with a filter layer having the same optical properties as first dichroic beam splitter (50) and/or as second dichroic beam splitter (51). The reflection element (54) may be provided with a filter layer having the same optical properties as first dichroic beam splitter (50). The reflection element (58) and/or (59) may be provided with a filter layer having the same optical properties as third dichroic beam splitter (56).

Further, reflection element (52) and/or reflection element (53) may be provided with a filter layer having the same optical properties as second dichroic beam splitter (51).

In addition, the microscope device of the invention may be provided with at least one focusing element (2) into the beam-path of the sample beam in order to create an image (6). In alternative (as shown in FIG. 2), the least one focusing element (2) may be provided into the beam-path of the image L and/or K. The focusing element (2) may consist or comprise at one lens or at least one objective or a combination thereof.

In case the respective dichroic beam splitters are long-pass filters, a short-pass filter can replace the bandpass, if the dichroic beam splitter is a short-pass, one needs long-pass filter.

The microscope device according to the present invention allows to differentiate the image of a color-labelled object with respect to up to four spectral regions, both in fluorescence-emission and in transmitted light absorption. Preferable. the optical path-lengths are identical for all spectral ranges (color-channels) and all images lie in the plane of the respective detector chip (camera).

This holds for an optimally corrected optical system. In the real world, the optical layout may be used to correct for longitudinal color-imperfections by adjusting the optical path-lengths accordingly.

In an unstained sample or for a transmitted or reflected light image, however, a volitional detuning of the path-lengths may be used to look at two or more focal depths simultaneously and to reconstruct contrast-enriched images from images taken at different focal positions. For example, a dichroic ensemble, designed for separating the emission excited by a 405 and a 488 nm laser, divides the light of a white light emitting diode into two spectral regions below and above 488 nm.

By suppressing ghost-images in the longer wavelength-channel >488 nm by inserting a optical element (22) into the beam-path (11), and by providing means to remove the optical element (22) from the beam, the thickness of the optical element (22) determines the path-length difference of beams A and B. The same arrangement can be provided with optical element (21), (23) and/or (24).

With a 40× objective, removing a filter-substrate of thickness 2 mm, provides a focal displacement the two images recorded by camera chip (109) of 416 nm. Obviously other means for providing a suitable path-length difference between two or more color channels are also possible according to the invention.

USE OF DEVICE

The microscope devices of the invention are especially useful in methods for detecting multiple spectral ranges which are emitted during sequencing of DNA/RNA molecules, in particular for sequencing-by-synthesis processes to obtain DNA or RNA sequence information of a biological sample.

Preferable, the sequencing-by-synthesis process is performed by hybridization of nucleotides provided with different dyes to the DNA or RNA of the biological sample and wherein the dyes emit light upon excitation by the one or more light sources in the spectral ranges A, B, C and D or combinations thereof. Such sequencing-by-synthesis process and the required dyes are known to the person skilled in the art

The invention claimed is:

1. A microscope device comprising:
   a microscope objective (1); one or more light sources; at least 3 dichroic beam splitters (50, 51, 56) and at least 2 cameras (109, 117) characterized in that the light generated by the light source interacts with the sample (3) thereby producing a sample beam (6), wherein
   sample beam (6) is divided with a first dichroic beam splitter (50) into beam (K) and beam (L) wherein beam (K) and beam (L) have different spectral ranges of light and wherein
   beam (K) is divided with a second dichroic beam splitter (51) into a first beam (A) having a first spectral range of light and a second beam (B) having a second spectral range of light and wherein first beam (A) is guided via reflection element (54) on the detector of the first camera (109) and wherein second beam (B) is guided via reflection elements (52) and (53) on the detector of the first camera (109) and wherein
   beam (L) is divided with a third dichroic beam splitter (56) into a third beam (C) having a third spectral range of light and a fourth beam (D) having a fourth spectral range of light and wherein third beam (C) is guided via reflection element (58) and (59) on the detector of the second camera (117) and wherein the fourth beam (D) is guided via reflection element (57) on the detector of the second camera (117).

2. The microscope device according to claim 1 characterized in that the tilt angles of first, second and third dichroic beam splitter (50, 51, 56) with the respective beams are independently between +45° and −45°.

3. The microscope device according to claim 1 characterized in that reflection element (54) is provided with a filter layer having the same optical properties as first dichroic beam splitter (50).

4. The microscope device according to claim 1 characterized in that reflection element (58) and/or (59) is provided with a filter layer having the same optical properties as third dichroic beam splitter (56).

5. The microscope device according to claim 1 characterized in that reflection element (52) and/or reflection element (53) is provided with a filter layer having the same optical properties as first dichroic beam splitter (50).

6. The microscope device according to claim 1 characterized in that reflection element (52) and/or reflection element (53) is provided with a filter layer having the same optical properties as second dichroic beam splitter (51).

7. The microscope device according to claim 1 characterized in that the light source provides light having a spectral range of 300 to 1750 nm.

8. The microscope device according to claim 1 characterized in providing at least one focusing element (2) into the beam-path of the sample beam (6).

9. The microscope device according to claim 8 characterized in that the focusing element (2) comprises at least one lens or at least one objective or a combination thereof.

10. The microscope device according to claim 1 characterized in providing one or more optical element (21, 22, 23, 24) into the beam-path of first, second, third and/or fourth beam A, B, C, D.

11. The microscope device according to claim 10 characterized in that the optical elements are capable of being inserted and removed from the beam-paths.

12. The microscope device according to claim 1 characterized in that the sample beam (6) comprises fluorescence or phosphorenscence radiation or transmitted light or reflected light originating from the sample (3).

13. The microscope device according to claim 1 characterized in that the first and second beam and/or the third and fourth beam originate from different positions on the sample (3); wherein the beams of the different positions are brought in alignment by moving the sample (3) relative to the cameras.

14. A use of the Microscope device according to claim 1 in a sequencing-by-synthesis process.

15. The use of the Microscope device according to claim 14 in a sequencing-by-synthesis process to obtain DNA or RNA sequence information of a biological sample.

16. The use of the microscope device according to claim 14 characterized in that the sequencing-by-synthesis process is performed by hybridization of nucleotides provided with different dyes to the DNA or RNA of the biological sample and wherein the dyes emit light upon excitation by the one or more light sources in the spectral ranges A, B, C and D or a combination thereof.

* * * * *